US011174468B2

(12) United States Patent
San et al.

(10) Patent No.: US 11,174,468 B2
(45) Date of Patent: Nov. 16, 2021

(54) GALACTOSE UTILIZATION

(71) Applicant: WILLIAM MARSH RICE UNIVERSITY, Houston, TX (US)

(72) Inventors: Ka-Yiu San, Houston, TX (US); Ping Liu, Houston, TX (US); Sha Li, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 121 days.

(21) Appl. No.: 16/092,042

(22) PCT Filed: Apr. 6, 2017

(86) PCT No.: PCT/US2017/026463
§ 371 (c)(1),
(2) Date: Oct. 8, 2018

(87) PCT Pub. No.: WO2017/177071
PCT Pub. Date: Oct. 12, 2017

(65) Prior Publication Data
US 2019/0119686 A1    Apr. 25, 2019

Related U.S. Application Data

(60) Provisional application No. 62/320,274, filed on Apr. 8, 2016.

(51) Int. Cl.
*C12N 9/12* (2006.01)
*C12P 7/64* (2006.01)
*C12N 1/20* (2006.01)
*C12N 15/00* (2006.01)
*C12N 15/70* (2006.01)
(Continued)

(52) U.S. Cl.
CPC .......... *C12N 9/1205* (2013.01); *C12N 15/52* (2013.01); *C12N 15/70* (2013.01); *C12N 15/74* (2013.01); *C12P 7/6409* (2013.01); *C12Y 207/01006* (2013.01); *C12N 1/20* (2013.01); *C12P 1/04* (2013.01); *Y02E 50/10* (2013.01)

(58) Field of Classification Search
CPC .................................................. C12N 9/1025
See application file for complete search history.

(56) References Cited

U.S. PATENT DOCUMENTS 7,709,261 B2   5/2010   San et al.
7,901,924 B2   3/2011   San et al.
(Continued)

FOREIGN PATENT DOCUMENTS

WO  PCT/US2017/026463    10/2017

OTHER PUBLICATIONS

Li. A highly efficient galactokinase from Bifidobacterium infantis with broad substrate specificity. Carbohydrate Research 355 (2012) 35-39.*

(Continued)

*Primary Examiner* — Yong D Pak
(74) *Attorney, Agent, or Firm* — Boulware & Valoir

(57) ABSTRACT

The present disclosure describes a genetically engineered bacteria that relieves the catabolite repression problem exerted by the Spot 42 small regulatory RNA by adding a galactokinase that does not contain the Spot 42 binding region. As such, galK and galM and the like can be expressed allow better galactose utilization.

18 Claims, 8 Drawing Sheets
Specification includes a Sequence Listing.

Spot 42 RNA (encoded by *spf*) act as an antisense RNA that mediates discoordinate expression of the *gal* operon

(51) Int. Cl.
*C12N 15/74* (2006.01)
*C12N 15/52* (2006.01)
*C12P 1/04* (2006.01)

(56) References Cited

U.S. PATENT DOCUMENTS

| | | |
|---|---|---|
| 8,236,525 B2 | 8/2012 | San et al. |
| 8,486,686 B2 | 7/2013 | Segueilha et al. |
| 8,709,753 B2 | 4/2014 | San et al. |
| 8,795,991 B2 | 8/2014 | San et al. |
| 8,906,667 B2 | 12/2014 | San et al. |
| 2014/0093921 A1 | 4/2014 | San et al. |
| 2014/0193867 A1 | 7/2014 | San et al. |
| 2014/0212935 A1 | 7/2014 | San et al. |
| 2014/0273114 A1 | 9/2014 | San et al. |

OTHER PUBLICATIONS

Citron. Expression of the yeast galactokinase gene in *Escherichia coli*. Gene. 6 (1979) 251-264.*

"List of sequenced bacterial genomes," accessed at en.wikipedia.org/wiki/List_of_sequenced_bacterial_genomes, last modified on May 11, 2019, pages.

Lim, H.G., et al., "Modular design of metabolic network for robust production of n-butanol from galactose-glucose mixtures," Biotechnology for Biofuels, vol. 8, No. 137, p. 8 (Sep. 4, 2015).

Moller, T., et al., "Spot 42 RNA mediates discoordinate expression of the *E. coli* galactose operon," Genes Dev. vol. 16, No. 13, pp. 1696-1706 (Jul. 1, 2002).

Tatusova, T.A. and Madden, T.L., "BLAST 2 Sequences, a new tool for comparing protein and nucleotide sequences," FEMS Microbiology Letters 174(2): 247-250, May 15, vol. 174, No. 2, pp. 247-250 (May 15, 1999) (Abstract).

Vorgias, C.E., et al., "Overexpression and purification of the galactose operon enzymes from *Escherichia coli*," Protein Expr Purif. vol. 2, No. 5-6, pp. 330-338 (Oct.-Dec. 1991) (Abstract).

Wang, X., et al., "Two-level inhibition of galK expression by Spot 42: Degradation of mRNA mK2 and enhanced transcription termination before the galK gene," Proc nat. Acad Sci. vol. 112, No. 24, pp. 7581-7586 (Jun. 16, 2015).

* cited by examiner

FIGURE 2

GALACTOSE UTILIZATION

PRIOR RELATED APPLICATIONS

This application claims priority to PCT/US2017/026463, filed Apr. 6, 2017, and U.S. Ser. No. 62/320,274, filed Apr. 8, 2016, each incorporated by reference herein in its entirety for all purposes.

FEDERALLY SPONSORED RESEARCH STATEMENT

Not Applicable.

FIELD OF THE DISCLOSURE

The invention relates to microbial production of products using genetically engineered bacteria with improved ability to utilize galactose as a carbon source. This is particularly beneficial, as galactose-containing feed sources are cheap and readily available, reducing the overall cost of using microbes for production of various products.

BACKGROUND OF THE DISCLOSURE

Engineering microorganisms for efficient production of chemicals, such as fats, feedstocks, and biofuels, from a mixture of sugars in a cheap feedstock is a prerequisite to achieve economic feasibility in any biorefinery. However, production of products from inedible and cheap feedstock is highly challenging due to the slower utilization of biomass-driven sugars, arising from complex assimilation pathway, difficulties in amplification of biosynthetic pathways for heterologous metabolites, and redox imbalance caused by consuming intracellular reducing power to produce reduced products. Thus, refactoring microorganisms for efficient conversion of various sugars into a useable product is highly desirable.

One abundant sugar in cheap feedstocks is galactose, mainly obtainable as a mixture of glucose from agar and cellulosic components of soybean, red seaweed, lactose of dairy waste, etc. Galactose is a C-4 epimer of glucose wherein the only difference is the orientation of the hydroxyl group on the fourth carbon. However, the pathway for galactose assimilation in microorganisms is more complicated than glucose. This leads to a more reduced rate for galactose utilization than that of glucose. In addition, the carbon catabolite repression (CCR) for selective utilization of glucose hinders the simultaneous utilization of galactose and glucose, and lowers the overall carbon flux toward central carbon metabolism. This is problematic because the microorganism factory should show robust performance with multiple carbohydrates regardless of carbon composition.

Galactose transport and metabolism in *Escherichia coli* involves a multicomponent amphibolic pathway. Galactose transport is accomplished by two different galactose-specific transport systems. At least four of the genes and operons involved in galactose transport and metabolism have promoters containing similar regulatory sequences. These sequences are recognized by at least three regulators, Gal repressor (GalR), Gal isorepressor (GalS) and cAMP receptor protein (CRP), which modulate transcription from these promoters. The negative regulators, GalR and GalS, discriminate between utilization of the high-affinity (regulated by GalS) and low-affinity (regulated by GalR) transport systems, and modulate the expression of genes for galactose metabolism in an overlapping fashion. GalS is itself autogenously regulated and CRP dependent, while the gene for GalR is constitutive.

The gal operon of *E. coli* (FIGS. 1 and 2) consists of 4 structural genes: galE (epimerase), galT (galactose transferase), and galK (galactokinase), and galM (mutarotase, which converts alpha-aldose to the beta-anomer) which are transcribed from two overlapping promoters P1 and P2 upstream from galE.

Regulation of the operon is complex since the GalE product, an epimerase that converts UDP-glucose into UDP-galactose, is required for the formation of UDP-galactose for cell wall biosynthesis, in particular the cell wall component lipopolysaccharide, even when cells are not using galactose as a carbon/energy source.

The gal operon contains two operators, OE (for external) and OI (for internal). The former is just before the promoters (P1, P2) at −60, and the latter is just after the promoters and before galE at +55. Repression of gene expression works via binding of galR repressor molecules to the two operators. These GalR repressors dimerize, creating a loop in the DNA. The loop, as well as hindrance from the external operator, prevents RNA polymerase from binding to the promoter, and thus prevents transcription. When GalR binds as a dimer to the −60 site only, promoter P2 is activated, not repressed. This allows basal levels of GalE to be produced. In this state, promoter P1 is inactivated through interactions with the alpha subunit of RNA polymerase.

The gal operon is also controlled by CRP-cAMP, similarly to the lac operon. CRP-cAMP binds to the −35 region, promoting transcription from P1 but inhibiting transcription from P2. When cells are grown in glucose, basal level transcription occurs from P2.

Galactose utilization is thus highly regulated in most microbial cells. As noted above, in the presence of other preferred carbon sources, such as glucose, the expression of enzymes involved in galactose utilization will be repressed because of the catabolite repression.

There are several additional regulatory mechanisms that cells employ in this repression process. One particular mechanism is the use of Spot 42 small regulatory RNA (sRNA), which inhibits the translation of galK within the gal operon. Spot 42 (spj) sRNA (FIG. 1) is a regulatory non-coding bacterial small RNA encoded by the spf (spot forty-two) gene. Spf is found in gammaproteobacteria and the majority of experimental work on Spot 42 has been performed in *Escherichia coli* and recently in *Aliivibrio salmonicida*. In the cell, Spot 42 plays essential roles as a regulator in carbohydrate metabolism and uptake, and its expression is activated by glucose, but inhibited by the cAMP-CRP complex.

The Spot 42 sRNA is transcribed from a separate promoter and binds to messenger RNA targets through imperfect base pairing. The half-life of Spot 42 in vivo is 12 to 13 minutes at 37° C. When grown in media supplemented with glucose, each cell contains 100-200 Spot 42 copies. The corresponding level is however reduced 3-4-fold when cells are grown in succinate or when cAMP is added to cells grown in glucose.

Most existing approaches to increase galactose utilization to date have involved manipulations at the transcription level, such as the deactivation/knockout of the galR gene or overexpression of the whole galactose operon under a standard promoter system. However, this approach has been less than satisfactory, perhaps because of the multiplicity of regulatory points. In particular, because of the Spot 42 small regulatory RNA, attempts to overexpress the gal operon still need improvement.

Thus, what is needed in the art, are better bacteria and methods of improving galactose utilization.

SUMMARY OF THE DISCLOSURE

Disclosed herein are genetically engineered bacteria strains with improved galactose utilization. These engineered bacteria strains are Spot 42 positive (meaning they have the gene and use this repression system) in the wild-type or native state, but the Spot 42 catabolite repression is avoided with the introduction of a galactokinase (galK) gene from an organism that is Spot 42 negative (meaning it does not contain the Spot 42 binding region).

Thus, this approach targets expression at the translation step where the galK gene from another organism that lacks the regulatory region for binding of Spot 42 is introduced to the cell. As such, galK and galM can be expressed normally and the GalK enzyme can be expressed even under repressed conditions. Additionally, if the added exogenous galactokinase from another organism has better enzyme properties, such as lower Km and higher Kcat values, than the native version, even further improved galactose utilization can be achieved.

Although the endogenous gal operon can be removed, this is not necessary, as the gal operon will be turned off or repressed anyway, and to the extent that it is not, that will further improve galactose utilization. Further improvements can be had by deleting spf and/or galR from the modified bacteria.

Bacteria modified using this method have been demonstrated to improve galactose utilization rates, even in mixed sugar media.

The steps involved in constructing these high galactose utilization strains are simple, and include:

1. Amplification and cloning of appropriate Spot 42 negative galK gene into an expression vector, such as pTrc99a. Alternatively, the galK gene can be chemically synthesized from known DNA sequences. As yet another alternative, the wild type gene can be gene edited e.g, with CRISPR/CAS9 and similar gene editing systems to delete or mutate that portion of the GalK gene that binds to Spot 42 sRNA.

2. Confirmation of the DNA sequence of the Spot 42 negative galK; and,

3. If applicable, introduction of the expression vector carrying the desired Spot 42 negative galK gene into an appropriate host strain, and confirmation thereof. As another alternative, the new gene can be inserted into the genome by known techniques, or as already noted, the endogenous gene can be edited by homologous recombination or gene editing.

4. If desired, further improvements can be made as described herein.

The invention includes one or more of the following embodiments in and combination(s) thereof:

A recombinant bacteria, said bacteria having a Spot 42 (spf) regulatory system when wild type, and also expressing, preferably overexpressing, an exogenous galactokinase lacking a Spot 42 binding region.

A recombinant bacteria, said bacteria having a Spot 42 (spf) regulatory system when wild type, comprising an expression vector, preferably an inducible expression vector, encoding a galactokinase lacking a Spot 42 binding region.

A recombinant bacteria, said bacteria having a Spot 42 (spf) regulatory system when wild type, comprising a knockout mutation of an endogenous galactokinase and expressing or overexpressing a galactokinase lacking a Spot 42 binding region.

A recombinant bacteria comprising a knockout mutation of an endogenous galactokinase and having an expression vector, preferably an inducible expression vector, encoding a galactokinase lacking a Spot 42 binding region.

Any recombinant bacteria herein described, said bacteria being of an Enterobacteriaceae or Vibrionaceae, preferrably *Shigella, Klebsiella, Salmonella, Yersinia, Vibrio, Aliivibrio, Photobacterium* or *Grimontia*.

Any recombinant bacteria herein described, wherein the bacteria further comprise an overexpressed gal operon, and/or an overexpressed of GalE, GalT, GalK, GalP, GalM and phosphoglucomutase (pgm).

These bacteria can also have reduced activity of enzymes from competing to pathways, depending on the product of interest, such as pathways to make ethanol, lactate, formate, and the like.

A method of producing a product, comprising growing any recombinant bacteria herein described in a culture medium comprising galactose or mixed sugars including galactose, for a time sufficient to produce a product, and isolating the product. In one embodiment, the culture medium comprises recycled biowaste material including galactose, such as soymeal hydrolysate, whey, red seaweed, molasses, cellulosic feedstocks, and the like.

To the extent that the overexpressed genes are controlled by an inducible promoter, inducing agent is also added to the culture medium, typically when a certain level of cell growth has been achieved (e.g., OD 0.5).

If desired, the cells can be grown at first under aerobic conditions and then switched to microaerobic conditions (<5% 02) and/or anaerobic conditions. If anaerobic conditions are to be used, an adjustment period of microaerobic conditions can be beneficial.

This summary is provided to introduce a selection of concepts that are further described below in the detailed description. This summary is not intended to identify key or essential features of the claimed subject matter, nor is it intended to be used as an aid in limiting the scope of the claimed subject matter.

As used herein, a "galactokinase" is an enzyme (phosphotransferase; (EC:2.7.1.6) that facilitates the phosphorylation of α-D-galactose to galactose 1-phosphate at the expense of one molecule of ATP.

As used herein a "Spot 42 negative galactokinase" or similar phrase is an active galactokinase enzyme, whose gene/RNA will not bind to the Spot 42 RNA of the host species being used.

As used herein, "Spot 42" is a regulatory non-coding bacterial small RNA encoded by the spf (Spot forty-two) gene. The spf gene is highly conserved, and has been found in many bacterial species. See e.g., FIGS. 2 and 3.

Generally speaking, we have referenced protein names herein and included EC numbers for accurate identification, but it is understood that a change in protein activity can of course be affected by changing the gene. This provides clarity since the gene nomenclature can be widely divergent in bacteria, but the proteins are defined by their activities and EC numbers.

Once an exemplary protein is obtained, e.g., in *E. coli*, which is completely sequenced and which is the workhorse of genetic engineering and bioproduction, many additional examples proteins of similar activity can be identified by BLAST search. Further, every protein record is linked to a gene record, making it easy to design expression or overexpression vectors. Many of the needed enzymes are already available in vectors, and can often be obtained from cell depositories or from the researchers who cloned them. But, if necessary, new clones can be prepared based on available sequence information using RT-PCR techniques or chemical synthesis. Thus, it should be easily possible to obtain all of the needed enzymes for overexpression.

Another way of finding suitable proteins/genes for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein. In addition, many sites provide lists of proteins that all catalyze the same reaction.

Understanding the inherent degeneracy of the genetic code allows one of ordinary skill in the art to design multiple nucleotides that encode the same amino acid sequence. NCBI provides codon usage databases for optimizing DNA sequences for protein expression in various species. Using such databases, a gene or cDNA may be "optimized" for expression in *E. coli*, or other bacterial species using the codon bias for the species in which the gene will be expressed.

The pathways in a living system are generally made by transforming the microbe with an expression vector (preferably an inducible one) encoding one or more of the proteins, but the genes can also be added to the chromosome by recombineering, homologous recombination, and similar techniques. Where the needed protein is endogenous, as is the case in some instances, it may suffice as is, but it is usually overexpressed using an inducible promoter for better functionality and user-control over the level of active enzyme.

The term "endogenous" means that a gene or protein originated from the species in question, without regard to subspecies or strain, although that gene may be naturally or intentionally mutated, or placed under the control of a promoter that results in overexpression or controlled expression of said gene. Thus, genes from Clostridia would not be endogenous to *Escherichia*, but a plasmid expressing a gene from *E. coli* or would be considered to be endogenous to any genus of *Escherichia*, even though it may now be overexpressed. The term "native" refers to a wild type endogenous gene or protein.

"Expression vectors" are used in accordance with the art-accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expressions vectors also exist.

As used herein, "inducible" means that gene expression can be controlled by the hand-of-man, by adding e.g., a ligand to induce expression from an inducible promoter. Exemplary inducible promoters include the lac operon, inducible by IPTG, the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressible, and preferably is inducible as well.

Initial cloning experiments may have proceeded in *E. coli* for convenience since most of the required genes were already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella*, and *Streptococcus*, or any of the completely sequenced bacterial species. Indeed, thousands of bacterial genomes have been completely sequenced, and this information greatly simplifies both the generation of vectors encoding the needed genes, as well as the planning of a recombinant engineering protocol. Such species are listed along with links at en.wikipedia.org/wiki/List_of_sequenced_bacterial_genomes, incorporated by reference herein in its entirety for all purposes.

Furthermore, a number of databases include vector information and/or a repository of vectors and can be used to choose vectors suitable for the chosen host species. See e.g., AddGene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues. Each of these databases is incorporated by reference herein in its entirety for all purposes.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ one or more expression plasmids hosting 3 or more ORFs for convenience, but it may be preferred to insert operons or individual genes into the genome for stability reasons.

Still further improvements in yield can be made by removing competing pathways, such as those pathways for making e.g., acetate, formate, ethanol, and lactate, and it is already well known in the art how to reduce or knockout these pathways. See e.g., the inventors' prior patents.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova TA & Madden TL (1999) FEMS Microbiol. Lett. 174:247-250, and available through the NCBI website. The default parameters were used, except the filters were turned OFF.

As used herein, the expressions "cell", "cell line" and "cell culture" are used interchangeably and all such designations include progeny. Thus, the words "cells" and similar designations include the primary subject cell and cultures derived therefrom without regard for the number of generation. It is also understood that all progeny may not be precisely identical in DNA content, due to deliberate or inadvertent mutations that arise after engineering is concluded. Mutant progeny that have the same function or biological activity as screened for in the originally transformed cell are included. Where distinct designations are intended, it will be clear from the context. Furthermore, reference to "a" cell typically includes cultures of that cell, which is common usage in the art.

As used herein, reference to a "cell" is generally understood to include a culture of such cells, as the work described herein is done in cultures having $10^{9-15}$ cells.

As used herein, "growing" cells has its art accepted manner, referring to exponential growth of a culture of cells, not the few cells that may not have completed their cell cycle at stationary phase or have not yet died in the death phase or after harvesting.

As used in the claims, "homolog" means an enzyme with at least 40% amino acid identity to one of the listed sequences and also having the same general catalytic activity, although the $K_m$ and $K_{cat}$ can vary. While higher identity (60%, 70%, 80%) and the like may be preferred, it is typical for bacterial sequences to diverge significantly (40, 50, 60%), yet still be identifiable as homologs, while mammalian species tend to diverge less (80-90%).

The terms "operably associated" or "operably linked," as used herein, refer to functionally coupled nucleic acid sequences.

As used herein, the term "engineered" means an organism being recombinantly modified to change its genetics in a particular way to achieve a particular result.

As used herein "recombinant" or "recombinant engineering" is relating to, derived from, or containing genetic material intentionally modified by the hand of man. In other words, the genetics were intentionally manipulated by the hand-of-man in some way.

By "metabolically modified", we refer to random mutagenesis and selective pressure to evolve an organism in a desired direction. Such procedures are often employed after a recombinant engineering step to further improve production of a desired product.

"Reduced activity" or "inactivation" or "down-regulated" is defined herein to be at least a 75% reduction in protein activity, as compared with an appropriate control species, and can be indicated by a negative superscript, e.g., GalK−. Preferably, at least 80, 85, 90, 95% reduction in activity is attained, and in the most extreme embodiment, the activity is eliminated (100%). Proteins can be inactivated with inhibitors, by mutation, or by suppression of expression or translation, and the like.

The terms "disruption" as used herein, refer to cell strains in which the native gene or promoter is mutated, deleted, interrupted, or down regulated in such a way as to decrease the activity of the protein at least 90% over the wild type un-disrupted protein. A gene or protein can be completely (100%) reduced by "knockout" or removal of the entire genomic DNA sequence. A "knockout" or "null" mutant can be represented by the Δ symbol.

Use of a frame shift mutation, early stop codon, point mutations of critical residues, or deletions or insertions, and the like, can completely inactivate (100%) gene product by completely preventing transcription and/or translation of active protein.

"Overexpression" or "overexpressed" is defined herein to be at least 150% of protein activity as compared with an appropriate control species or as having detectable expression of a gene not normally present in that host, and can be indicated by a positive superscript, e.g, Spot 42 negative GalK+. Overexpression can be achieved by mutating the protein to produce a more active form, or a form that is resistant to inhibition, by removing inhibitors, or adding activators, and the like. Overexpression can also be achieved by removing repressors, adding multiple copies of the gene to the cell, or upregulating the endogenous gene, and the like. In contrast, "expression" refers to normal levels of activity or better.

Acid and base forms of a molecule are used interchangeably herein, thus use of butyrate is intended to and does include butanoic acid.

NAD+ and NADH are used interchangeably herein, since the reactions involved converting one to the other. Likewise, NADP+ and NADPH are used interchangeably.

An "NADPH-dependent" enzyme relies on NADPH as a cofactor, whereas an "NADH-dependent" enzyme uses NADH. An "NAD(P)H-dependent" enzyme can use either.

The use of the word "a" or "an" when used in conjunction with the term "comprising" in the claims or the specification means one or more than one, unless the context dictates otherwise.

'The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| ACP | acyl carrier protein |
| AMP | Ampicillin resistance |
| bi_galK | GalK from a *Bifidobacterium infantis* |
| bom | a region required in cis for plasmid transfer |
| CmR | chloramphenicol resistant gene |
| CCR | carbon catabolite repression |
| CoA | Coenzyme A |
| CRP | cyclic AMP receptor protein |
| ec | *E. Coli* |
| galE | Epimerase |
| galK | Galactokinase |
| galP | galactose MFS transporter |
| galR | gal repressor (unlinked to the gal operon) |
| galS | gal isorepressor |
| galT | galactose transferase |
| galM | galactose-1-epimerase (mutarotase) |
| IPTG | Isopropyl thiogalactoside |
| LacI | Lac operon repressor |
| LB media | Luria Broth media, commercially available |
| M9 media | M9 minimal media, commercially available |
| $O_E$ | External operator |
| $O_I$ | Internal operator |
| ori | Origen of replication |
| P1 | Promoter 1 |
| P2 | Promoter 2 |
| Pgm | phosphoglucomutase |
| Rrnb T1 terminator | terminator region from the *Escherichia coli* rrnB gene |

-continued

| ABBREVIATION | TERM |
|---|---|
| SPF | Spot 42 gene |
| TE | Thioesterase |
| Trc promoter | A Strong *E. coli* promoter hybrid between the trp (tryptophan) and lac UV5 (variant of the wild type *Escherichia coli* lac core promoter) promoters |

BRIEF DESCRIPTION OF DRAWINGS

Figure 2:
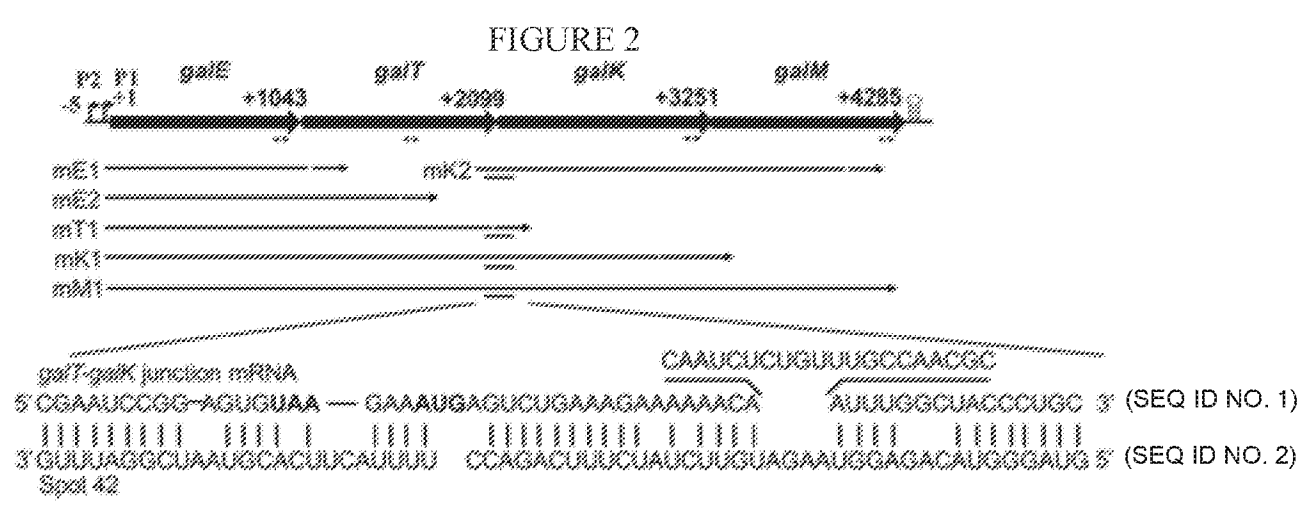

FIG. 2: Three gal operon and the mRNA species detected by Northern blot analysis (2) are presented as thick and thin lines, respectively. The numbers indicate the positions of the stop codon of each cistron from the transcription initiation sites of the P1 promoter. The left-right arrows (↔) indicate the primer sets for RT-qPCR. Note that the primer sets are at the 3' end of the respective genes, except in the case of galT. The stem and loop structure for the transcription termination of mM1 is presented at the end of the operon. The three short lines under the mK1, mM1, and mK2 mRNA species indicate the regions where Spot 42 binds. The sequence of Spot 42 and its binding site at the galT-galK cistron junction are shown with short vertical lines indicating base-pairing. The stop codon of galT and the start codon of galK are indicated in bold case. Hfq binds to the 3' end of Spot 42. The numbers indicate nucleotide positions. From Wang (2015).

FIG. 4: Plasmid pPL18-gal/bi_galK uses pTrc99a as backbone, carrying an acyl-ACP thioesterase gene from *Ricinus communis*, and five genes involved in galactose utilization (galP, pgm, galE, galT, galM) from *E. coli* and bi_galK from *Bifidobacterium infantis*.

FIG. 5: pPL18-gal/bi_galK uses pTrc99a as backbone, carrying an acyl-ACP thioesterase from *Ricinus communis* and fabZ, galP, pgm, galE, galT, galM, galK from *E. coli*.

FIG. 6: pTrc-bigalK was constructed from pTrc99a, carrying bigalK from *Bifidobacterium infantis*

FIG. 7: pTrc-gal operon was constructed from pTrc99a, carrying galE, galT, galM, galK from *E. coli*

FIG. 8: pTrc-gal/bi_galK was constructed from pTrc99a, carrying galE, galT, galM from *E. coli* and bi_galK from *Bifidobacterium infantis*.

DETAILED DESCRIPTION

The invention provides a novel method of making any bacterial product, utilizing a recombinant bacteria that has an added, exogenus Spot 42 negative galactokinase gene therein or wherein the endogenous gene has been modified to be spot 42 negative. The galK and galM in the gal operan can then be expressed normally and the GalK enzyme can be expressed even under repressed conditions.

The present described recombinant bacteria are exemplified with respect to the *E. Coli* strains listed in Table 1 and *Bacillus subtilis*. However, this is exemplary only, and the invention can be broadly applied to any bacteria strain that is applied in any species having a spf gene in its native or wild type state. The spf gene is highly conserved in *Escherichia, Shigella, Klebsiella, Salmonella, Yersinia* genera within the Enterobacteriaceae family. In *E. coli* the spf gene is flanked by polA (upstream) and yihA (downstream). A CRP binding sequence and −10 and −35 promoter sequences are found upstream of spf.

Spf is also highly conserved within the Vibrionaceae family, and was recently identified in all 76 available Vibrionaceae genomes (e.g., *Vibrio, Aliivibrio, Photobacterium* and *Grimontia* genera). In e.g., *Vibrio cholerae, Vibrio vulnificus, Aliivibrio fischeri* and *Aliivibrio salmonicida* the spf gene is flanked by polA (upstream) and a sRNA gene encoding the novel VSsRNA24 (downstream).

TABLE 1

Strains and gene information used in the examples

| Strain | Description or genotype |
|---|---|
| *E. coli* MG1655 | Wild type |
| *E. coli* ML103 | MG1655 ΔfadD |
| *E. coli* ML190 | MG1655 ΔfadDΔptsG |
| *E. coli* XZK009 | MG1655 ΔfadDΔptsGΔspf |
| *E. coli* SL103 | MG1655 ΔfadDΔgalR |
| *E. coli* SL190 | MG1655 ΔfadDΔptsGΔgalR |

Figure 1:
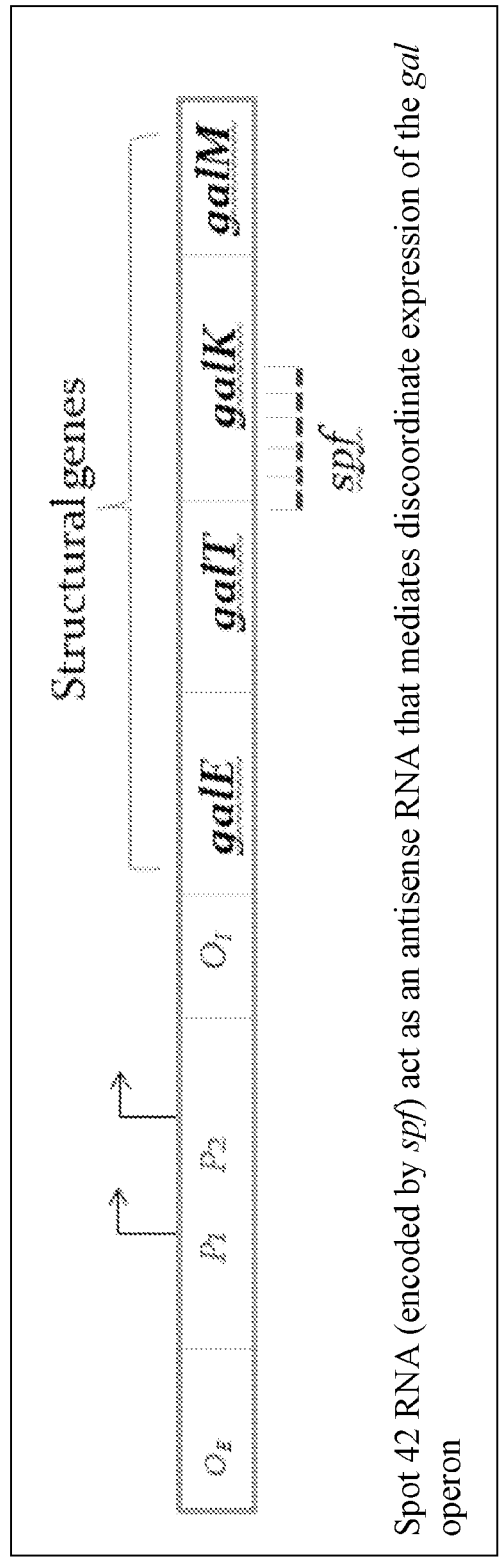
FIG. 1: Diagram showing the gal operon. The gal operon is a prokaryotic operon, which encodes enzymes necessary for galactose metabolism. The operon contains two operators, $O_E$ (for external) and $O_1$. The former is just before the promoter, and the latter is just before the galE gene (the first gene in the operon).
Figure 3:
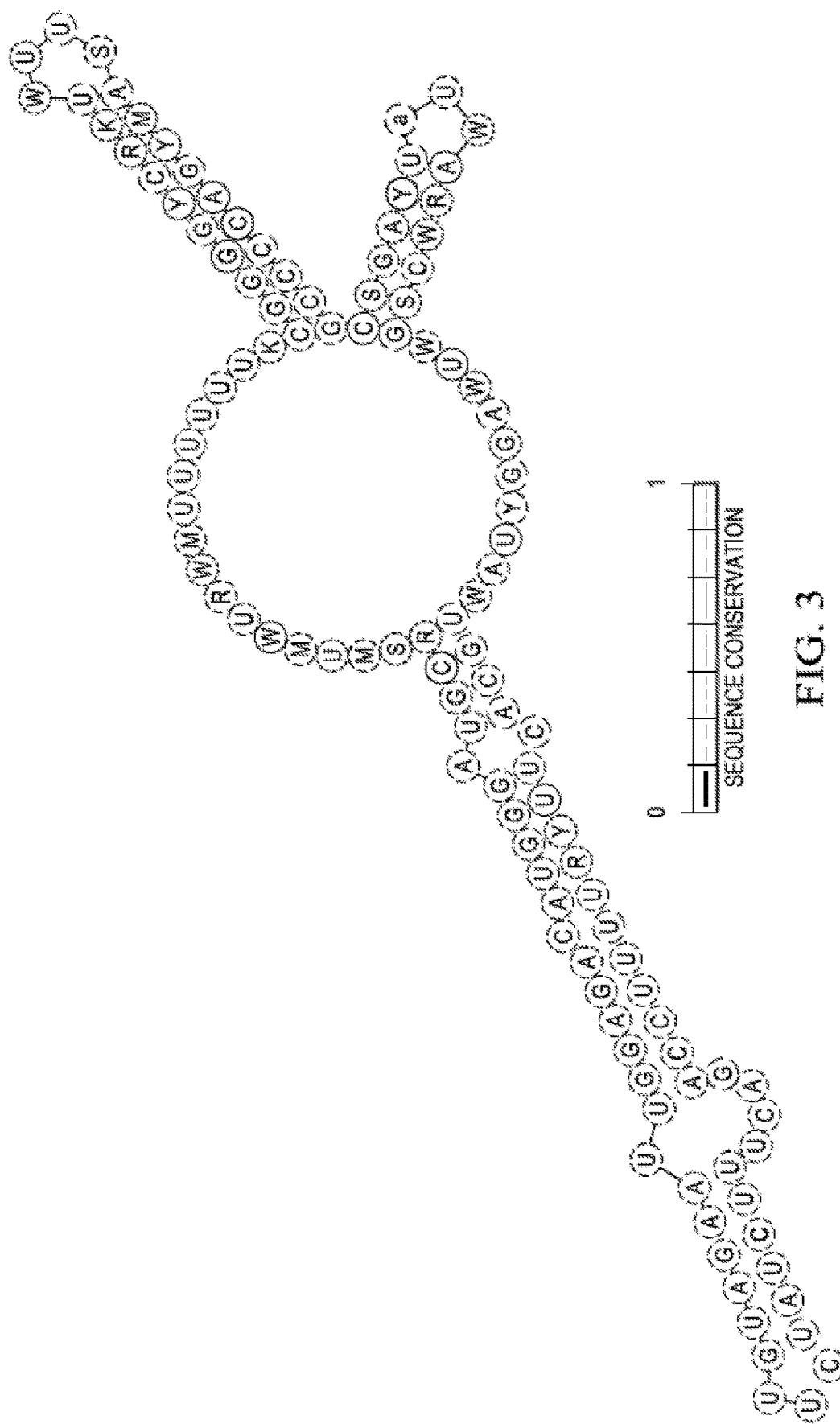
FIG. 3: Spot 42 RNA. Spot 42 can interact directly with mRNA targets through base pairing. Although now known to bind at least 14 different operons, the first Spot 42 targets a short complementary region at the translation initiation region of galK (encodes a galactokinase). galK is the third gene in the galactose operon, which contains four genes (galETKM) and produces a polycistronic mRNA. Spot 42 mediates discoordinate expression of the gal operon (i.e., the individual genes in the operon are not similarly expressed) by binding to the galK Shine-Dalgarno region, thereby blocking ribosome binding and translation of the galK gene. Data suggests that Spot 42 plays a role in fine-tuning gene expression to optimize the utilization of carbon sources.
Figure 4:
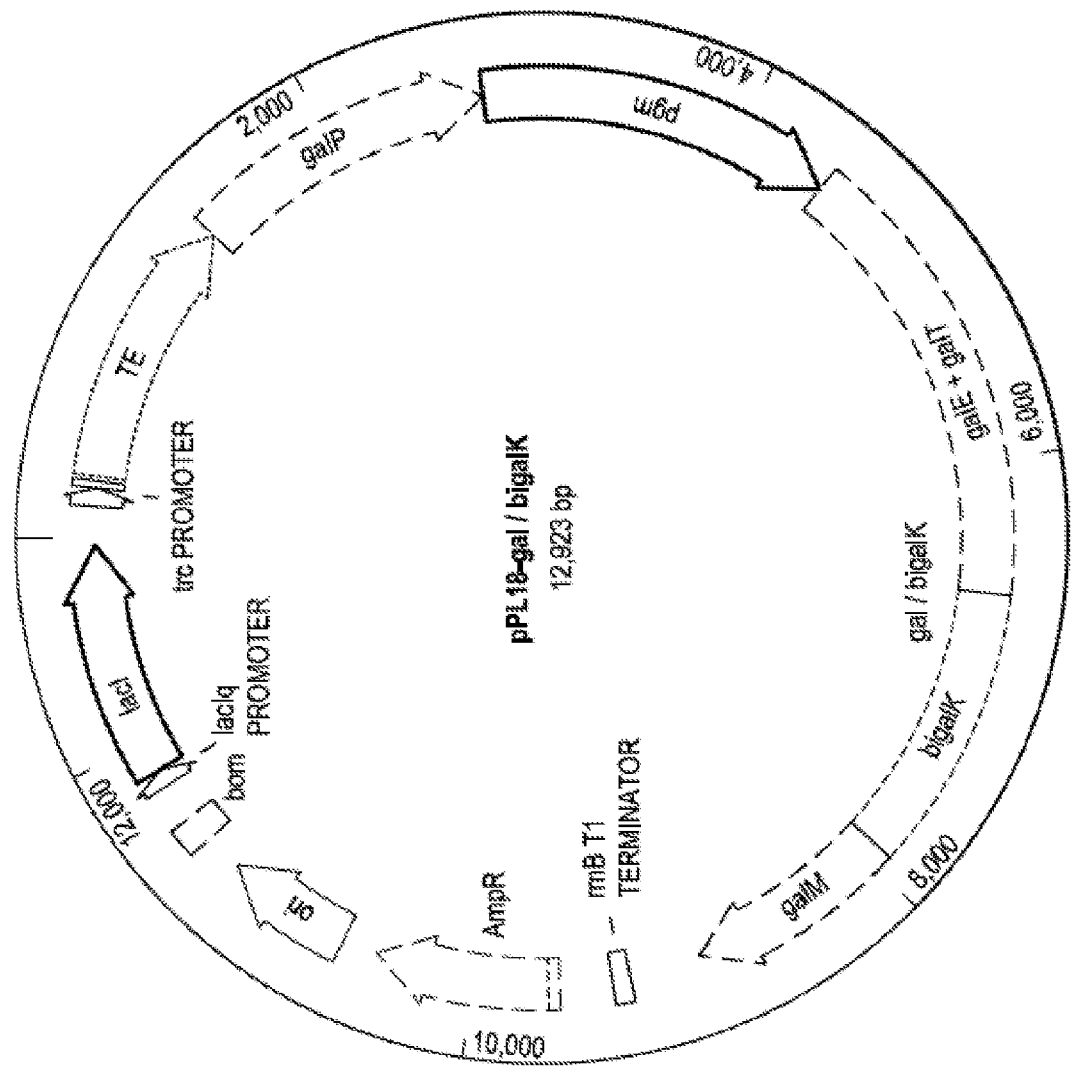
FIG. 4-8: Diagrams showing the various vector constructs used herein.
Figure 5:
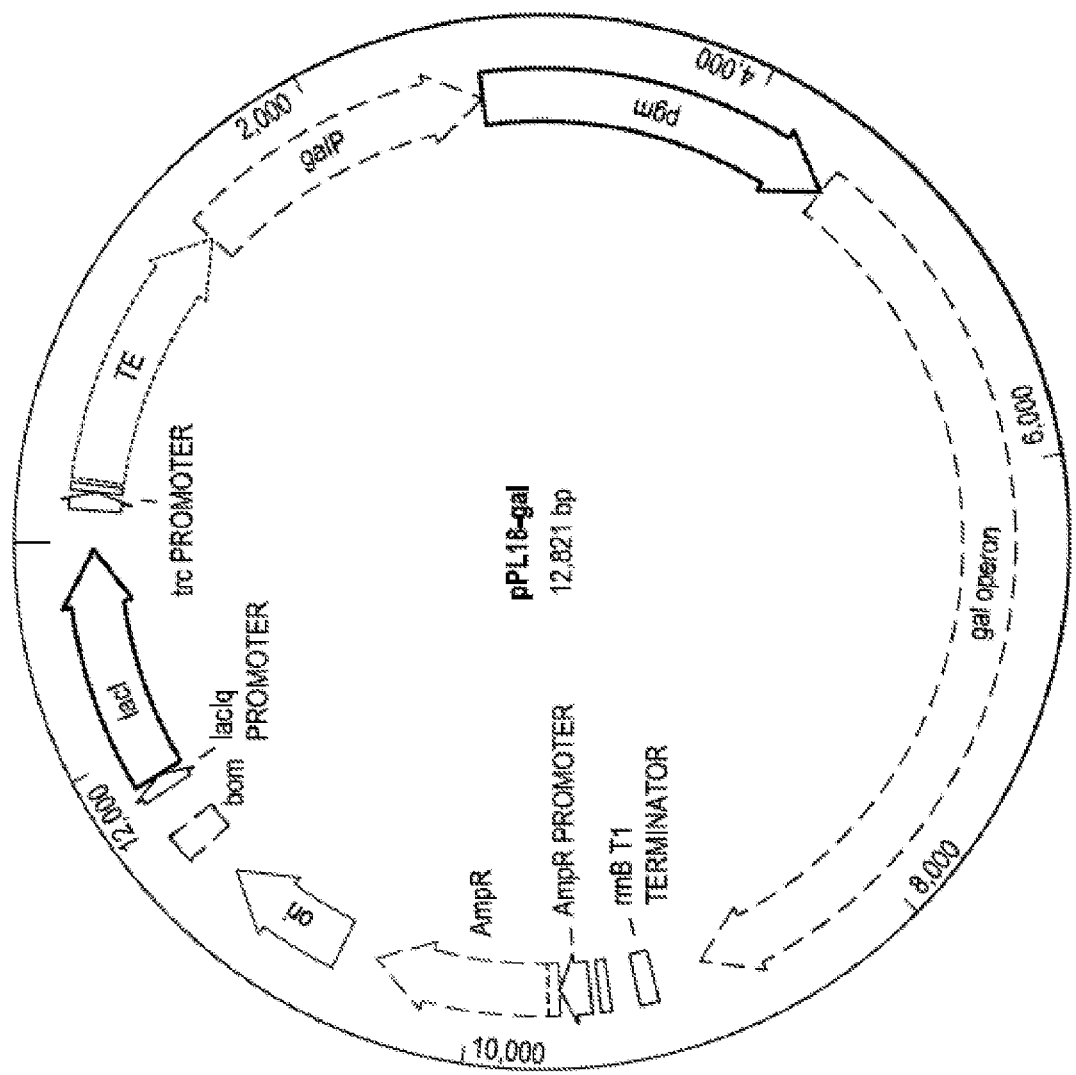
Figure 6:
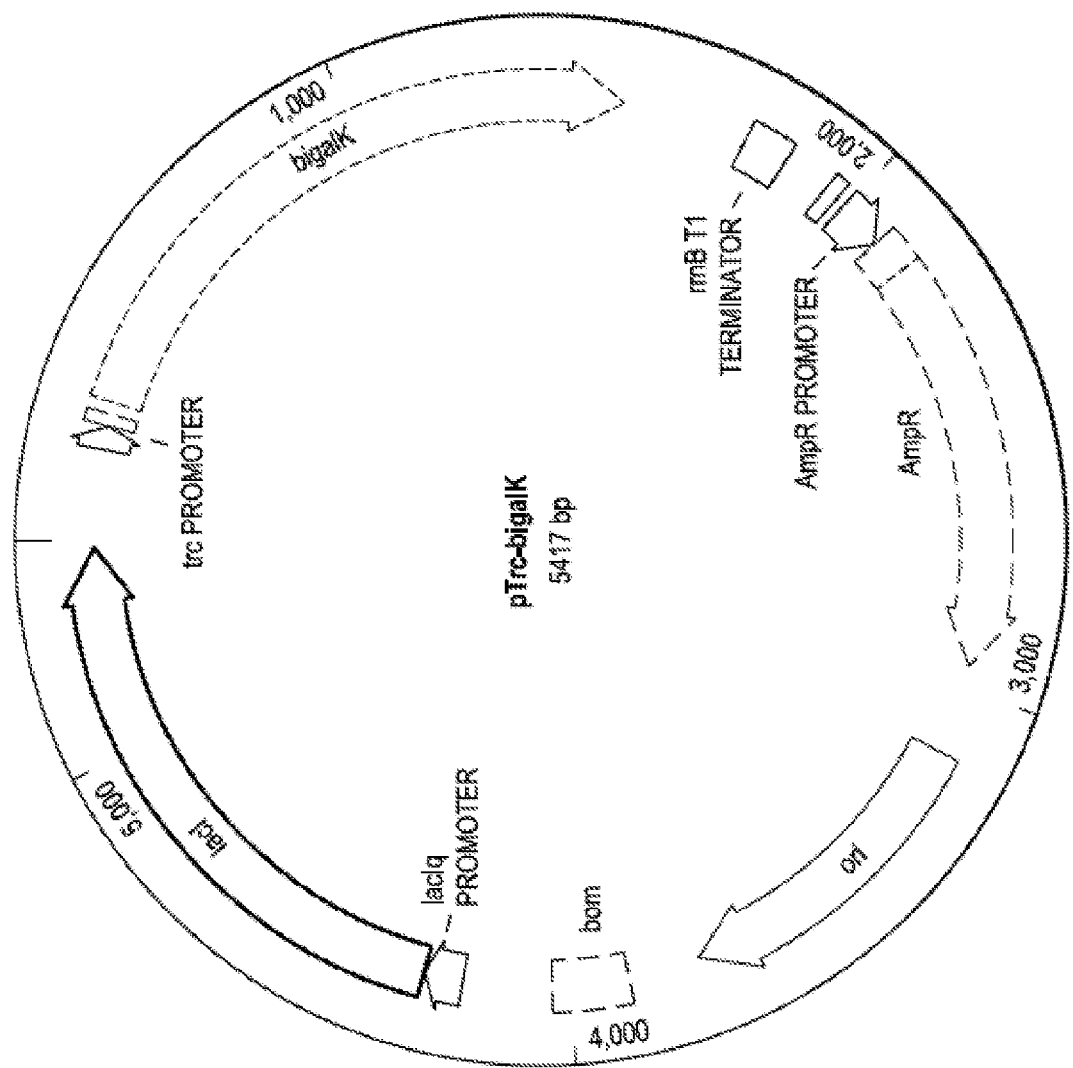
Figure 7:
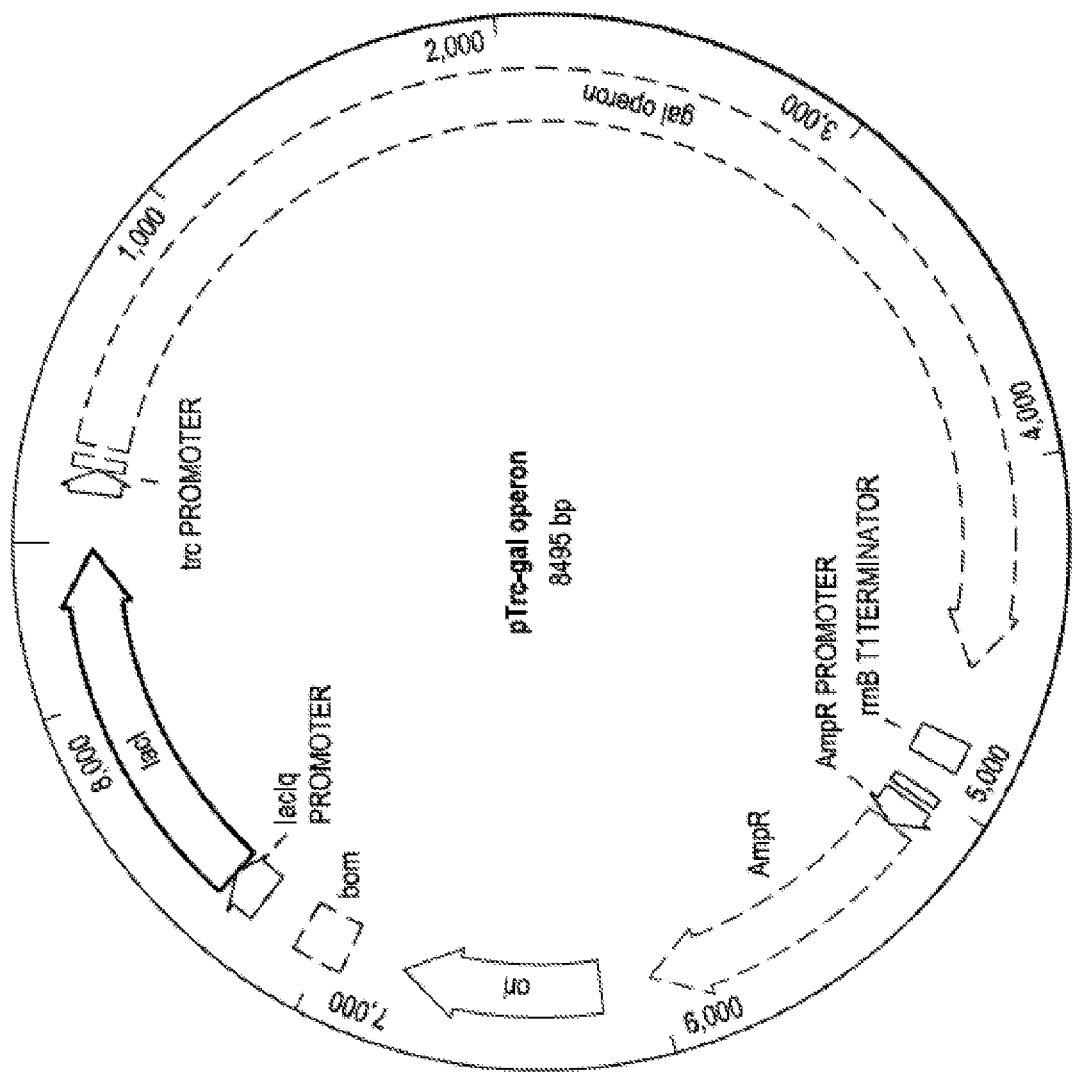
Figure 8:
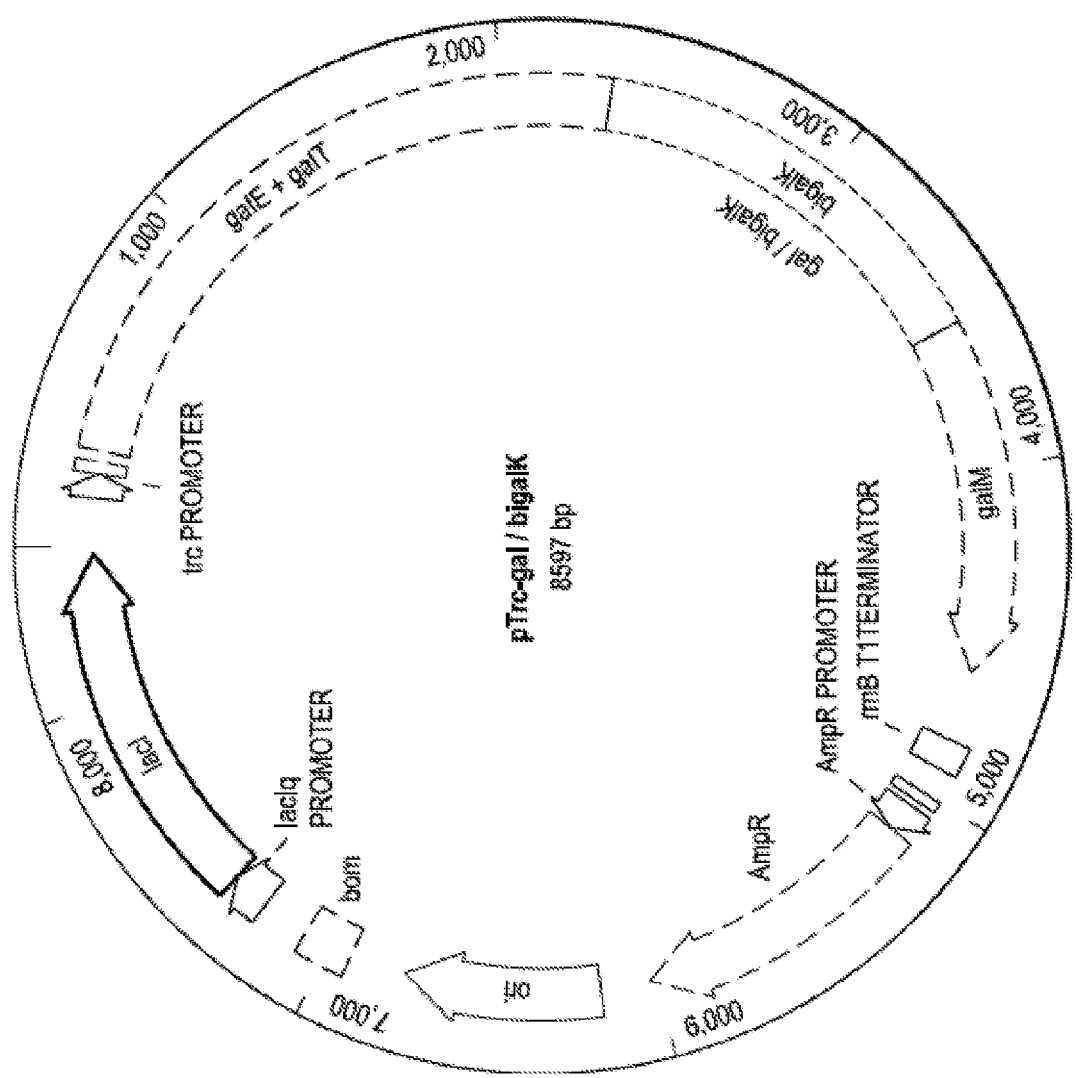

Exemplary vector constructs are shown in FIG. 4-8.

The following examples are intended to be illustrative only, and not unduly limit the scope of the appended claims.

Briefly, we constructed a plasmid named pTrc-gal/bi_g-alK that contained a galactokinase from *Bifidobacterium longum* subsp. *infantis* (bi_galK), which does not contain the Spot 42 binding region. This plasmid is an example of the type of exogenuous genes that can replace the native *E. coli* galK. This plasmid construct also carries the *E. coli* galE, galT and galM genes.

The use of a galactokinase from *Bifidobacterium longum* subsp. *infantis* (bi_galK) is just an example of the type of plasmid that can be created to combine with the bacteria strain. Other similar galK genes without the Spot 42 region can be used, such as those list in the Table 2. Further, as noted an endogenous gene can be gene edited to remove or mutate the Spot 42 binding region.

TABLE 2

Some examples of Spot 42-negative galactokinases (galK) from the following organisms that can be used, in addition to *Bifidobacterium infantis*, to replace *E. coli* galK

| Gene | Organism | GeneBank Access NO or Gene ID |
|---|---|---|
| atgalk | *Arabidopsis thaliana* | 819837 |
| gal1 | *Trichoderma reesei* | AY249022 |
| galKSpe4 | *Streptococcus pneumoniae* | AAK75925 |
| galK | *Streptococcus thermophilus* | AAU21544 |
| gal1 | *Saccharomyces cerevisiae* | 852308 |

To demonstrate the effectiveness of using a galactokinase that does not contain the Spot 42 binding region for galactose utilization in engineered bacteria, we performed experiments using this pTrc-gal/bi_galK construct. We found that strains carrying the pTrc-gal/bi_galK outperform the galactose utilization in those bacteria carrying the native galK both in galactose only medium, as well as in medium containing a mixture of sugars (glucose and galactose).

Additionally, using fatty acid as the targeted product, strains carrying the pTrc-gal/bi_galK produce more fatty acids than those carrying the native galK in galactose only medium and in soymeal hydrolysate, which contains galactose as a major sugar component.

The production of fatty acids as an exemplary target product is an example of one means to monitor the abilities of the recombinant bacteria, but the same technology can be used in producing other products from galactose. A more detailed description of our experiments are below.

Cultivation Method

First, we cultivated a colony of cells with the Spot 42 negative galK gene. A single colony of strain MG1655 (pTrc99a), MG1655 (pTrc-bi_galK), MG1655 (pTrc-gal operon) or MG1655 (pTrc-gal/bi_galK) was inoculated into 5 ml of Luria-Bertani (LB) and incubated in an orbital shaker operated at 250 rpm at 37° C. overnight. The pre-culture was inoculated into a flask containing 50 mL of the culture medium with 1% (v/v) inoculum. The culture medium contained: tryptone 10 g/L, yeast extract 5 g/L, NaCl 5 g/L, galactose 15 g/L, ampicillin 100 µg/L, pH 7.5 supplemented with 1 mM IPTG.

Shake flask experiments were performed at 30° C. with shaking at 250 rpm for 72 h. The samples were taken at 24 and 48 hours after inoculation. Galactose utilization (g/L) was monitored using an HPLC. Fatty Acid production levels were also monitored using GC or GC/MS.

These cultivation conditions were generally employed throughout the experiments, with modification as noted.

Bi_Galk & Galactose Utilization

Four strains, MG1655 (pTrc99a), MG1655 (pTrc-bi_galK), MG1655 (pTrc-gal operon) or MG1655 (pTrc-gal/bi_galK) were examined for their ability to utilize galactose. In addition, the effect of different inducer (IPTG) concentration on galactose utilization for this series of plasmids was studied to determine the optimal induction level. The results for these experiments are summarized in Table 3.

All strains showed the highest galactose utilization at the end of 48 hours at 0.025 mM IPTG. The strain carrying the plasmid pTrc-gal/bi_galK (a Spot 42 negative galactokinase) consumed 10.51 g/L of galactose. This is about 10% better than the strain carrying the plasmid pTrc-gal operon expressing the native E. coli galactose operon.

Our experimental data indicated that the optimal induction level is around 0.025 mM IPTG. Further, replacing the native E. Coli GalK with a GalK from a Bifidobacterium infantis (bi_galK) that lacks the Spot 42 binding region improved galactose utilization by more than 10%.

TABLE 3

Galactose utilization under different IPTG concentrations in MG1655 harboring different plasmid constructs

| Strain | Relevant genotype | IPTG (mM) | Galactose utilization (g/L) 24 h | Galactose utilization (g/L) 48 h |
|---|---|---|---|---|
| bi_galK+: overexpression of galK from *Bifidobacterium infantis* in pTrc99a ec_GalETKM+: overexpression of galETKM from *Escherichia coli* in pTrc99a | | | | |
| MG1655 (pTrc-bi_galK) | bi_GalK+ | 0 | 3.07 | 2.81 |
| | | 0.025 | 1.79 | 5.33 |
| | | 0.05 | 1.87 | 1.87 |
| | | 0.1 | — | — |
| | | 0.2 | 1.67 | 1.16 |
| MG1655 (pTrc-gal operon) | ec_GalE+ ec_GalT+ ec_GalK+ ec_GalM+ | 0 | 4.59 | 7.12 |
| | | 0.025 | 3.60 | 7.91 |
| | | 0.05 | 3.20 | 7.09 |
| | | 0.1 | 2.77 | 6.36 |
| | | 0.2 | 2.11 | 5.16 |
| MG1655 (pTrc-gal/bi_galK) | ec GalE+ ec GalT+ ec GalM+ bi_GalK+ | 0 | 4.38 | 6.65 |
| | | 0.025 | 4.09 | 10.51 |
| | | 0.05 | 3.89 | 9.82 |
| | | 0.1 | 3.67 | 9.94 |
| | | 0.2 | 3.35 | 8.53 |

Bi_Galk & Different Genetic Backgrounds

A series of experiments were also performed with two different host E. coli strains to demonstrate that the genetic background was not controlling. Strain ML190 is a ptsG mutant and strain XZKO09 is a ptsG, spf double mutant. The results are summarized in Table 4.

TABLE 4

Galactose utilization by a series of gal constructs in host strain ML190, SL190 and XZK009

| Strain | Relevant genotype | IPTG (mM) | Galactose utilization (g/L) 24 h | Galactose utilization (g/L) 48 h |
|---|---|---|---|---|
| Bi_galK+: overexpression of galK from *Bifidobacterium infantis* in pTrc99a ec_GalETKM+: overexpression of galETKM from *Escherichia coli* in pTrc99a | | | | |
| ML190 (pTrc99a) | ΔfadDΔptsG | 0.025 | 3.05 | 4.01 |
| ML190 (pTrc-bi_galK) | bi_galK+ | | 1.67 | 6.65 |
| ML190 (pTrc-gal operon) | ΔfadDΔptsG ec GalE+ ec GalT+ eccGalK+ ec GalM+ | | 2.62 | 7.17 |
| ML190 (pTrc-gal/bi_galK) | ΔfadDΔptsG ec GalE+ ec GalT+ ec GalM+ bi_galK+ | | 1.59 | 9.92 |
| SL190 (pTrc99a) | ΔfadDΔptsGΔgalR | 0.025 | 0 | 1.80 |
| SL190 (pTrc-bi_galK) | ΔfadDΔptsGΔgalR bi_galK+ | | 0 | 2.09 |
| SL190 (pTrc-gal operon) | ΔfadDΔptsGΔgalR ec GalE+ ec GalT+ ec GalK+ ec GalM+ | | 2.93 | 1.56 |
| SL190 (pTrc-gal/bi_galK) | ΔfadDΔptsGΔgalR ec GalE+ ec GalT+ ec GalM+ bi_galK+ | | 1.54 | 0.98 |

TABLE 4-continued

Galactose utilization by a series of gal constructs in host strain ML190, SL190 and XZK009

| Strain | Relevant genotype | IPTG (mM) | Galactose utilization (g/L) 24 h | 48 h |
|---|---|---|---|---|
| XZK009 (pTrc99a) | ΔfadDΔptsGΔspf | 0.025 | 2.78 | 3.98 |
| XZK009 (pTrc-bi_galK) | ΔfadDΔptsGΔspf bi_galK+ | | 1.28 | 6.34 |
| XZK009 (pTrc-gal operon) | ΔfadDΔptsGΔspf ec GalE+ ec GalT+ ec GalK+ ec GalM+ | | 0.81 | 6.97 |
| XZK009 (pTrc-gal/bi_galK) | ΔfadDΔptsGΔspf ec GalE+ ec GalT+ ec GalM+ bi_galK+ | | 7.11 | 11.71 |

Several observations can be made from the results in Table 4:

The ML190 (pTrc99a), carrying the cloning vector pTrc99a (see GenBank| M22744), utilized 4.01 g/L of galactose at 48 h; the ptsG, spf double mutant strain, XZK009 (pTrc99a), does not increase galactose utilization (3.98 g/L).

For the ptsG mutant strain ML190, overexpression of bi_galK only or the native gal operon, or replacing the native E. Coli GalK with bi_galK all improved galactose utilization from utilized 4.01 g/L to a high value of 9.92 g/L by the ML190 (pTrc-gal/bi_galK) strain, more than doubling the galactose utilization.

Similar observations were observed for the spf mutant strain XZKO09. Overexpression of bi_galK only or the native gal operon, or replacing the native ec GalK with bi_galK all improved galactose utilization from utilized 3.98 g/L to a high value of 11.71 g/L by the XZKO09 (pTrc-gal/bi_galK) strain, representing a tripling of the galactose utilization.

Thus, the experimental data indicated that replacing the native E. Coli GalK with a galactokinase without the Spot 42 binding region (such as galK from Bifidobacterium infantis—bi_galK) improves galactose utilization significantly. Additional deactivation of the Spot 42 gene (spf) further enhances the galactose utilization.

Bi_Galk & Mixed Sugars

A series of experiments were performed with the host strain ML190 carrying plasmids pTrc-bi_galK, pTrc-gal operon, and pTrc-gal/bi_galK. These experiments are designed to examine the ability of these strains to utilize galactose in a sugar mixture and the results are shown in Table 5. The ability to utilize galactose from a sugar mixture is highly desirable because many cheap or recycled feedstocks are a mix of sugars.

TABLE 5

Galactose utilization of mixed sugar medium by ML190 carrying gal series plasmids

| Strain | Relevant genotype | IPTG (mM) | Galactose utilization (g/L) 24 h | 48 h | 72 h |
|---|---|---|---|---|---|
| ML190 (pTrc-bi_galK) | ΔfadDΔptsG bi_galK+ | 0.025 | 0/3.04 | 0.78/6.51 | 1.68/6.38 |
| ML190 (pTrc-gal operon) | ΔfadDΔptsG ec GalE+ ec GalT+ ec GalK+ ec GalM+ | | 0.27/1.9 | 1.75/4.96 | 3.40/6.78 |
| ML190(pTrc-gal/bi_galK) | ΔfadDΔptsG ec GalE+ ec GalT+ ec GalM+ bi_galK+ | | 0.72/3.19 | 3.31/6.97 | 6.57/6.99 |

Bi_galK+: overexpression of galK from Bifidobacterium infantis in pTrc99a ec GalETKM+: overexpression of GalETKM from Escherichia coli in pTrc99a In this set of experiments, the ML190 (pTrc-gal/bi_galK) strain performed the best. The experimental data in Table 5 indicated that replacing the native E. Coli galK with a galK from Bifidobacterium infantis (bi_galK) improves galactose utilization significantly.

Bi_Galk & Improved Productivity from Galactose

Another means of characterizing the recombinant bacteria disclosed herein is by monitoring their ability to form or synthesize certain products. Here, we used medium chain length fatty acids as a marker for characterizing the improvement in productivity over native or wild type bacteria.

The synthesis of medium chain length fatty acids was used to demonstrate the use of bi_galK to improve galactose utilization and fatty acid production. SL103 was used as the host strain.

Three plasmids were examined, plasmid pXZ18 carrying only an acyl-ACP thioesterase from Ricinus communis (rc TE), plasmid pPL18-gal carrying the galactose operon from E. coli in addition to the rc TE, and plasmid pPL18-gal/bi_galK carrying the galactose operon from E. coli with the GalK replaced by bi_galK in addition to the rc TE. The results are summarized in Table 6.

TABLE 6

Fatty acid production by strain SL103 in galactose

| Strain | Relevant genotype | IPTG (mM) | Concentration of total fatty acid (g/L) 24 h | 48 h | 72 h | Galactose utilization (g/L) 24 h | 48 h | 72 h |
|---|---|---|---|---|---|---|---|---|
| SL103 (pXZ18) | rc_TE+ | 0.025 | 0.79 | 1.03 | 1.06 | 5.91 | 8.27 | 10.02 |

TABLE 6-continued

Fatty acid production by strain SL103 in galactose

| Strain | Relevant genotype | IPTG (mM) | Concentration of total fatty acid (g/L) | | | Galactose utilization (g/L) | | |
|---|---|---|---|---|---|---|---|---|
| | | | 24 h | 48 h | 72 h | 24 h | 48 h | 72 h |
| SL103 (pPL18-gal) | ΔfadDΔgalR ec GalE+ ec GalT+ ec GalK+ ec GalM+ ec GalP+ ec Pgm+ | | 0.95 | 1.24 | 1.23 | 2.55/ | 7.43 | 7.98 |
| SL103 (pPL18-gal/bi_galK) | ΔfadDΔgalR ec GalE+ ec GalT+ bi_galK+ ec GalM+ ec GalP+ ec Pgm+ | | 0.33 | 1.82 | 2.10 | 0.58/ | 7.87 | 12.45 | rc_TE+: overexpression of acyl-ACP thioesterase from *Ricinus communis* under the PTRC promoter in pTrc99a
bi_galK+: overexpression of bi_galK from *Bifidobacterium infantis* in pTrc99a
ec GalETKM+: overexpression of galETKM from *Escherichia coli* in pTrc99a
ec GalP+: overexpression of galP from *Escherichia coli* in pTrc99a
ec Pgm+: overexpression of pgm from *Escherichia coli* in pTrc99a The strain SL103 (pXZ18) served as the control and it produced 1.02 g/L of fatty acids at 72 h. The SL103 (pPL18-gal) strain with overexpression of the native galactose operon improved the fatty acid production by about 20% to 1.23 g/L. The SL103 (pPL18-gal/bi_galK) strain with the bi_galK improved the fatty acid production significantly; a two-fold increase to 2.10 g/L was obtained when compared with the control strain, SL103 (pXZ18).

Thus, this set of experiments, using production of fatty acids as an exemplary product, demonstrated that the use of a galactokinase without the Spot 42 binding region can significantly improve product production. Again, other fatty acids or synthesis products can also be used as benchmarks to monitor the improvement of galactose utilization.

Bi_Galk & Soymeal Hydrolysate

To determine how well the recombinant bacteria were able to utilize galactose from a sugar mixture, a soymeal hydrosolyate was added to the culture process.

Carbohydrates from soymeal hydrolysate provide an inexpensive carbon source. Further, soymeal hydrolysate contains a mixture of sugars, but the major components are glucose, fructose and galactose.

As before, the synthesis of medium chain length fatty acids was used as a benchmark to demonstrate the use of bi_galK to improve galactose utilization and fatty acid production from soymeal hydrolysate. Similar to above, SL103 was used as the host strain. Three plasmids were examined, plasmid pXZ18 carrying only an acyl-ACP thioesterase from *Ricinus communis* (rc TE), plasmid pPL18-gal carrying the galactose operon from *E. coli* in addition to the rc TE, and plasmid pPL18-gal/bi_galK carrying the galactose operon from *E. coli* with the galK replaced by bi_galK in addition to the rc TE. The results are summarized in Table 7.

TABLE 7

Fatty acid production by strain SL103 using soymeal hydrolysate

| Strain | Relevant genotype | IPTG (mM) | Concentration of total fatty acid (g/L) | | |
|---|---|---|---|---|---|
| | | | 24 h | 48 h | 72 h |
| | rc_TE+: overexpression of acyl-ACP thioesterase from *Ricinus communis* under the Ptrc promoter in pTrc99a bi_galK+: overexpression of bi_galK from *Bifidobacterium infantis* in pTrc99a ec GalE+: overexpression of galE from *Escherichia coli* in pTrc99a ec GalT+: overexpression of galT from *Escherichia coli* in pTrc99a ec GalK +: overexpression of galK from *Escherichia coli* in pTrc99a ec GalM +: overexpression of galM from *Escherichia coli* in pTrc99a ec GalP +: overexpression of galP from *Escherichia coli* in pTrc99a ec Pgm +: overexpression of pgm from *Escherichia coli* in pTrc99a | | | | |
| SL103 (pXZ18) | ΔfadDΔgalR rc_TE+ | 0.025 | 0.64 | 1.43 | 1.36 |
| SL103 (pPL18-gal) | ΔfadDΔgalR ec GalE+ ec GalT+ ec GalK+ ec GalM+ ec GalP+ ec Pgm+ | | 0.49 | 0.65 | 1.07 |
| SL103 (pPL18-gal/bi_galK) | ΔfadDΔgalR ec GalE+ ec GalT+ bi_galK+ ec GalM+ ec GalP+ ec Pgm+ | | 1.02 | 1.57 | 1.61 |

The strain SL103 (pXZ18), which served as the control, produced 1.36 g/L of fatty acids at 72 h. The SL103 (pPL18-gal) strain with overexpression of the native galactose operon did not perform well; this strain only produce 1.07 g/L. However, the SL103 (pPL18-gal/bi_galK) strain with the bi_galK improved the fatty acid production to 1.61 g/L, an 18% improvement over that of the control strain, SL103 (pXZ18).

Thus, this set of experiments, using production of fatty acids as an example, further demonstrated that the use of a galactokinase without the Spot 42 binding region can significantly improve product production from soymeal carbohydrate hydrolysate containing a mixture of sugars.

Prophetic: Bacillus

The above experiments were repeated in Bacillus subtilis cells.

The same genes can be used, especially since Bacillus has no significant codon bias. A protease-deficient strain like WB800N is preferably used for greater stability of heterologous protein. The E. coli-B. subtilis shuttle vector, pMTLBS72, exhibited full structural stability and was used to move the genes easily to a more suitable vector for Bacillus. Alternatively, two vectors pHT01 and pHT43 allow high-level expression of recombinant proteins within the cytoplasm. As yet another alternative, plasmids using the theta-mode of replication such as those derived from the natural plasmids pAMβ1 and pBS72 can be used. Several other suitable expression systems are available.

Since the GAL genes are ubiquitous, the modified Bacillus performed as expected.

U.S. Pat. No. 8,236,525 Reduced phosphotransferase system activity in bacteria
U.S. Pat. No. 7,901,924 Increased bacterial CoA and acetyl-CoA pools
U.S. Pat. No. 7,709,261 Recycling system for manipulation of intracellular NADH availability
Møller, T., et al., Spot 42 RNA mediates discoordinate expression of the E. coli galactose operon, Genes Dev. 2002 Jul. 1; 16(13): 1696-1706.
Lim, H. G., et al., Modular design of metabolic network for robust production of n-butanol from galactose-glucose mixtures, Biotechnology for Biofuels 20158:137 (2015).
Vorgias C. E., et al., Overexpression and purification of the galactose operon enzymes from Escherichia coli. Protein Expr Purif. 1991 October-December; 2(5-6):330-8.
Wang, X., et al., Two-level inhibition of galK expression by Spot 42: Degradation of mRNA mK2 and enhanced transcription termination before the galK gene, Proc. nat. Acad. Sci. 112(24): 7581-7586 (2015).

All GenBank, UniProt accession numbers or gene ID numbers referenced herein are incorporated by reference herein in its entirety for all purposes.

SEQUENCE LISTING

```
<160> NUMBER OF SEQ ID NOS: 2

<210> SEQ ID NO 1
<211> LENGTH: 74
<212> TYPE: RNA
<213> ORGANISM: Artificial Sequence
<220> FEATURE:
<223> OTHER INFORMATION: Sense 5'-3' galT-galK junction mRNA

<400> SEQUENCE: 1
cgaauccgga guguaagaau gagucugaaa gaaaaaacac aaucucuguu ugccaacgca      60
uuuggcuacc cugc                                                        74

<210> SEQ ID NO 2
<211> LENGTH: 61
<212> TYPE: RNA
<213> ORGANISM: Artificial Sequence
<220> FEATURE:
<223> OTHER INFORMATION: antisense 5'-3' galT-galK junction mRNA

<400> SEQUENCE: 2
guaggguaca gagguaagau guucuaucuu ucagaccuuu uacuucacgu aaucggauuu      60
g                                                                      61
```

The following references are incorporated by reference in their entirety for all purposes:
U.S. Pat. No. 8,906,667 Increasing NADPH-dependent products
US20140273114 Bacteria and method for synthesizing fatty acids
U.S. Pat. No. 8,795,991 Increasing bacterial succinate productivity
US20140212935 Short chain fatty acids from bacteria
US20140193867 Microbial odd chain fatty acids
U.S. Pat. No. 8,709,753 Native NAD-dependent GAPDH replaced with NADP-dependent GAPDH plus NADK
US20140093921 Bacteria and method for synthesizing fatty acids
U.S. Pat. No. 8,486,686 Large scale microbial culture method

The invention claimed is:

1. A recombinant bacteria, said bacteria being from a gammaproteobacterial species having a Spot 42 (spf) responsive galactokinase (GalK) when said species is wild type at GalK, and said bacteria comprising:
   a) a knockout mutation of an endogenous spot 42 responsive GalK; and
   b) expressing an open reading frame (ORF) from a GalK lacking a Spot 42 binding region (GalK$^{Spot42-}$) under the control of a promotor that is not native to the GalK$^{Spot42-}$;
   wherein said recombinant bacteria is able to avoid catabolite repression and grow on mixed sugars comprising galactose and glucose.

2. The recombinant bacteria of claim 1, wherein said mixed sugars comprising galactose and glucose comprises soymeal hydrolysate.

3. The recombinant bacteria of claim 1, said ORF being operably linked to an expression vector.

4. The recombinant bacteria of claim 1, said ORF being operably linked to an inducible expression vector.

5. The recombinant bacteria of claim 1, said ORF being operably linked to an constitutive expression vector.

6. The recombinant bacteria of claim 1, said species being selected from the group consisting of Enterobacteriaceae, Vibrionaceae, *Escherichia, Shigella, Klebsiella, Salmonella, Yersinia, Vibrio, Aliivibrio, Photobacterium* and *Grimontia*.

7. The recombinant bacteria of claim 1, said GalK$^{Spot42-}$ being an ORF selected from GalK$^{Spot42-}$ genes from *Bifidobacterium longum* subsp. *infantis, Arabidopsis thaliana, Trichoderma reesei, Streptococcus pneumonia, Streptococcus thermophilus* and *Saccharomyces cerevisiae*.

8. The recombinant bacteria of claim 1, said bacteria further comprising an overexpressed gal operon.

9. The recombinant bacteria of claim 1, said bacteria further comprising an expression vector that encodes a gal operon.

10. The recombinant bacteria of claim 1, said bacteria further comprising an inducible expression vector that encodes a gal operon.

11. The recombinant bacteria of claim 1, said bacteria further comprising overexpression of GalE, GalT, GalK, GalP and pgm.

12. The recombinant bacteria of claim 1, said bacteria further comprising an inducible expression vector encoding *E. coli* GalE, GalT, GalK, GalP and pgm.

13. A method of producing a fatty acid, comprising growing the recombinant bacteria of claim 1 in a culture medium comprising galactose and glucose for a time sufficient to produce a fatty acid, and isolating said fatty acid from bacteria, or said culture medium, or both.

14. A method of producing a fatty acid, comprising growing the recombinant bacteria of claim 11 in a culture medium comprising galactose and glucose for a time sufficient to produce a fatty acid, and isolating said fatty acid from bacteria, or said culture medium, or both.

15. A recombinant bacteria, said bacteria being a gammaproteobacterial species having a Spot 42 (spf) responsive GalK when said species is wild type at GalK, and said recombinant bacteria comprising:
   a) a knockout mutation of an endogenous spot 42 responsive GalK; and
   b) expressing a GalK$^{Spot42-}$ ORF from *Bifidobacterium* under a promoter that is not native to *Bifidobacterium;* wherein said bacteria is able to avoid catabolite repression and grow on mixed sugars comprising galactose and glucose.

16. The recombinant bacteria of claim 15, said bacteria further comprising overexpression of GalE, GalT, GalK, GalP and pgm.

17. A method of producing a fatty acid, comprising growing the recombinant bacteria of claim 16 in a culture medium comprising galactose and glucose for a time sufficient to produce a fatty acid, and isolating said fatty acid from bacteria, or said culture medium, or both.

18. The method of claim 17, wherein said culture medium comprises soymeal hydrolysate.

* * * * *